(12) United States Patent
Kim

(10) Patent No.: US 12,133,925 B2
(45) Date of Patent: Nov. 5, 2024

(54) STERILIZATION DEVICE

(71) Applicant: SUZHOU LEKIN SEMICONDUCTOR CO., LTD., Taicang (CN)

(72) Inventor: Dae Hun Kim, Seoul (KR)

(73) Assignee: SUZHOU LEKIN SEMICONDUCTOR CO., LTD., Suzhou (CN)

( * ) Notice: Subject to any disclaimer, the term of this patent is extended or adjusted under 35 U.S.C. 154(b) by 885 days.

(21) Appl. No.: 17/275,367

(22) PCT Filed: Sep. 20, 2019

(86) PCT No.: PCT/KR2019/012189
§ 371 (c)(1),
(2) Date: Mar. 11, 2021

(87) PCT Pub. No.: WO2020/060253
PCT Pub. Date: Mar. 26, 2020

(65) Prior Publication Data
US 2022/0047735 A1    Feb. 17, 2022

(30) Foreign Application Priority Data

Sep. 20, 2018  (KR) .................... 10-2018-0113331

(51) Int. Cl.
*A61L 2/10*      (2006.01)
*B66B 31/02*     (2006.01)

(52) U.S. Cl.
CPC ............ *A61L 2/10* (2013.01); *A61L 2202/11* (2013.01); *A61L 2202/12* (2013.01); *A61L 2202/15* (2013.01); *B66B 31/02* (2013.01)

(58) Field of Classification Search
None
See application file for complete search history.

(56) References Cited

U.S. PATENT DOCUMENTS

2018/0099842 A1    4/2018   Kim et al.

FOREIGN PATENT DOCUMENTS

| JP | 2016141551 A | * | 8/2016 |
| KR | 10-2009-0021821 A | | 3/2009 |
| KR | 20-2013-0002312 U | | 4/2013 |
| KR | 10-2013-0124026 A | | 11/2013 |

(Continued)

*Primary Examiner* — Andrew Smyth
(74) *Attorney, Agent, or Firm* — Birch, Stewart, Kolasch & Birch, LLP

(57) ABSTRACT

Disclosed is a sterilization device. One embodiment of the sterilization device comprises: a frame including a first coupling part, a second coupling part, and a first connection part for connecting the first coupling part and the second coupling part; a first circuit board disposed in the first coupling part; a second circuit board disposed in the second coupling part; a first ultraviolet light emitting element disposed on one surface of the first circuit board so as to face in a first direction; a second ultraviolet light emitting element disposed on one surface of the second circuit board so as to face in a second direction crossing the first direction; and a first wiring part connected to the second circuit board to supply power, wherein the first connection part includes a first through-hole through which the first wiring part passes.

20 Claims, 9 Drawing Sheets

(56) References Cited

FOREIGN PATENT DOCUMENTS

| KR | 20130124026 | A | * | 11/2013 |
| KR | 10-1362113 | B1 | | 2/2014 |
| KR | 10-1415154 | B1 | | 7/2014 |
| KR | 10-2017-0099499 | A | | 9/2017 |
| KR | 10-2017-0116506 | A1 | | 10/2017 |
| KR | 20170116506 | A | * | 10/2017 |
| KR | 10-1839510 | B1 | | 4/2018 |

* cited by examiner

[FIG. 1]
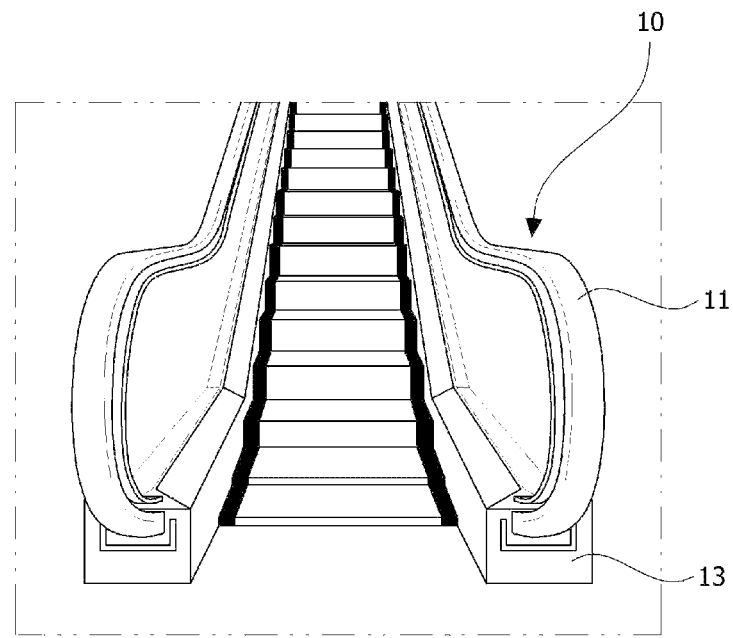
[FIG. 2]
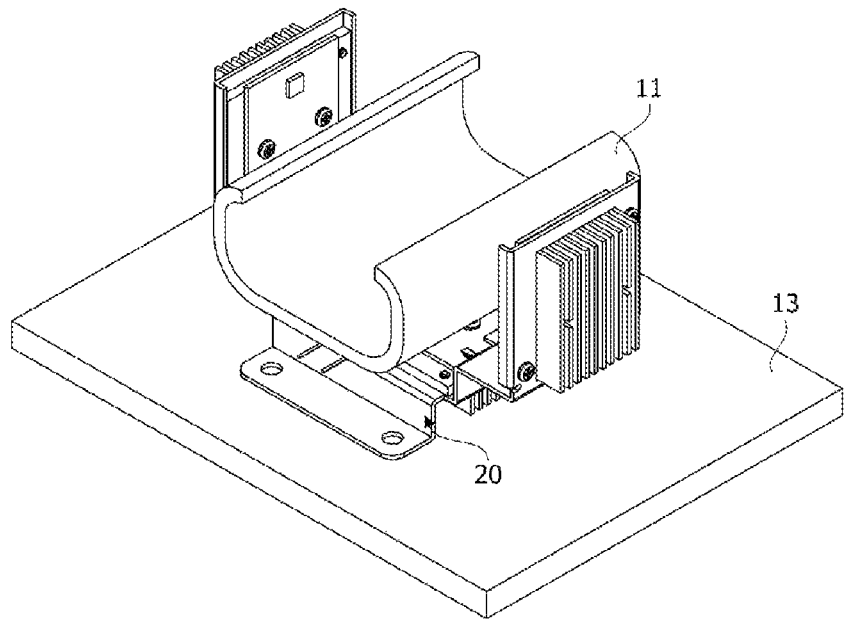

[FIG. 3]
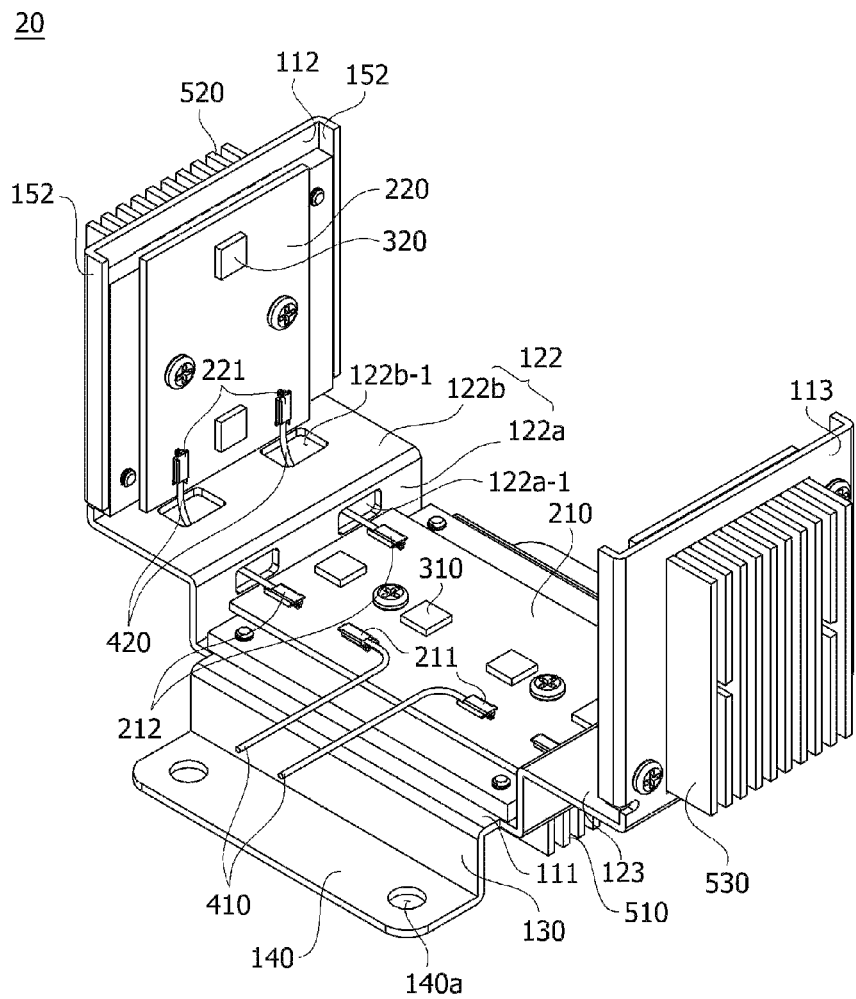

[FIG. 4]
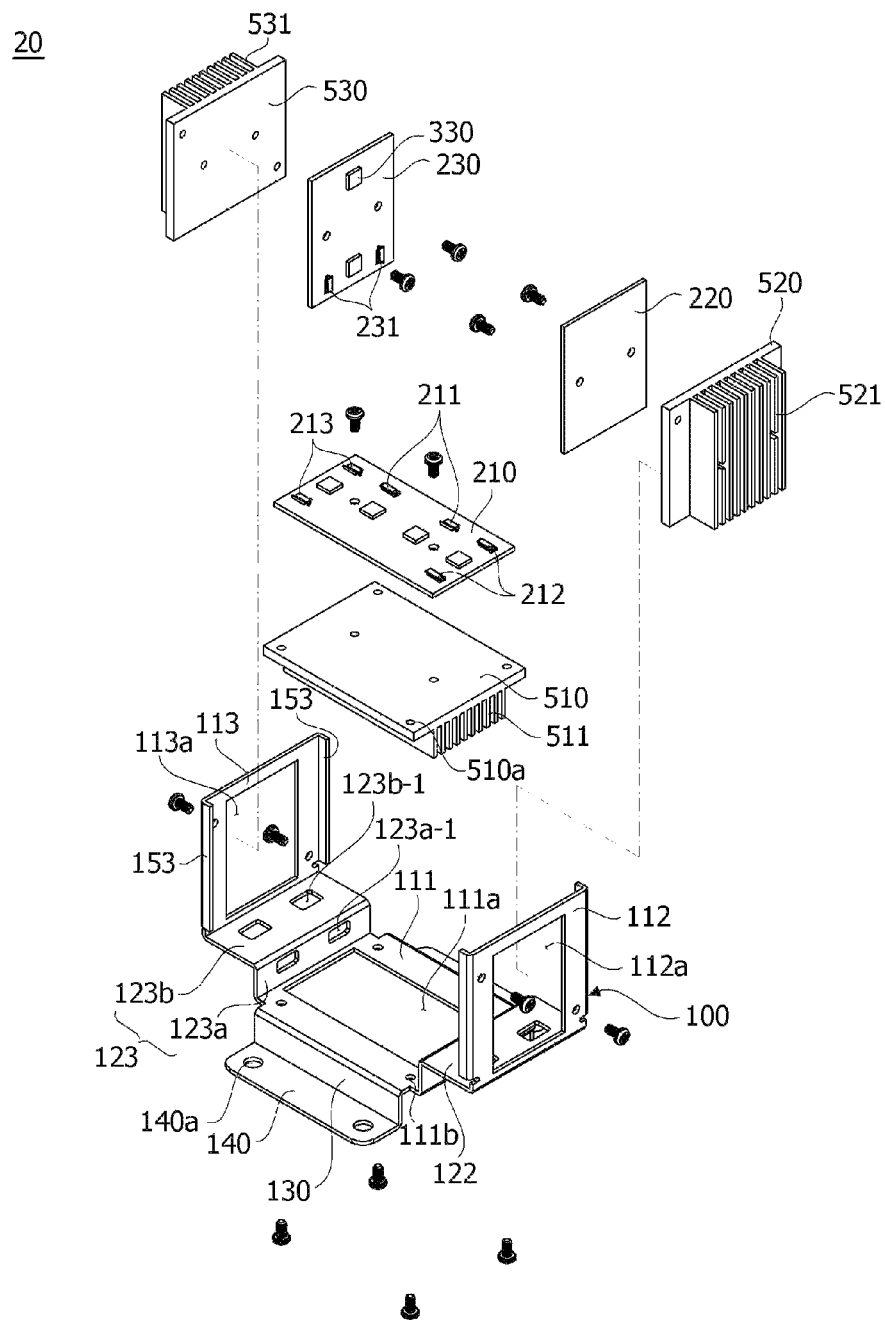

[FIG. 5]
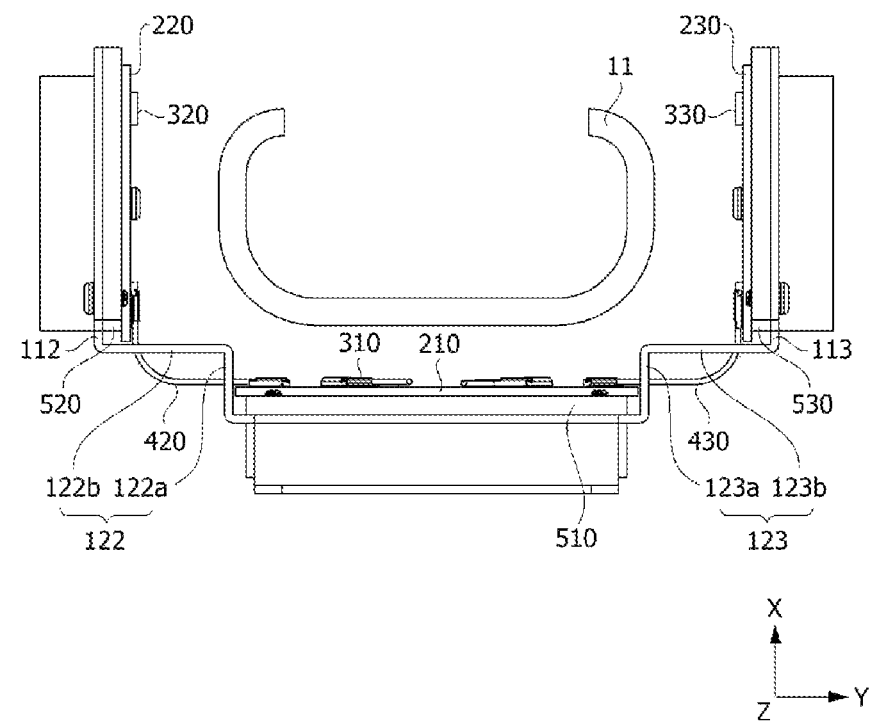
[FIG. 6]
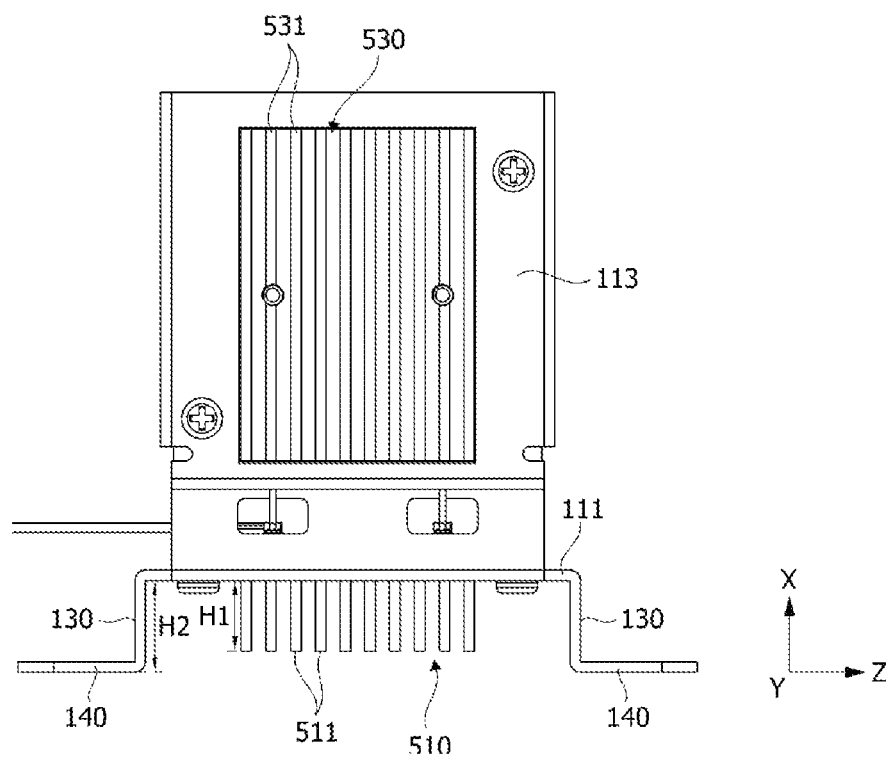

[FIG. 7]
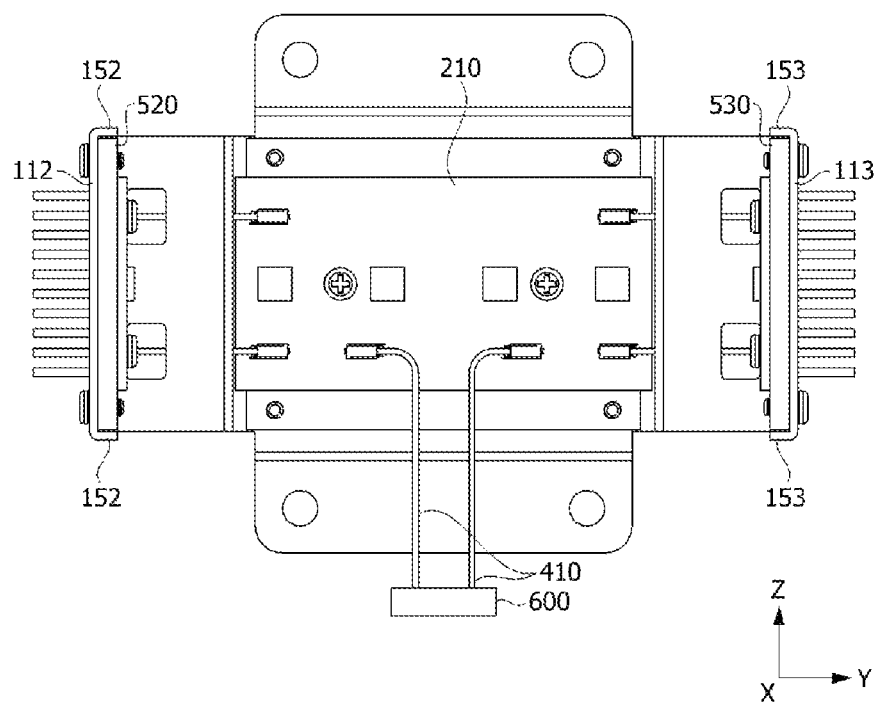

[FIG. 8]
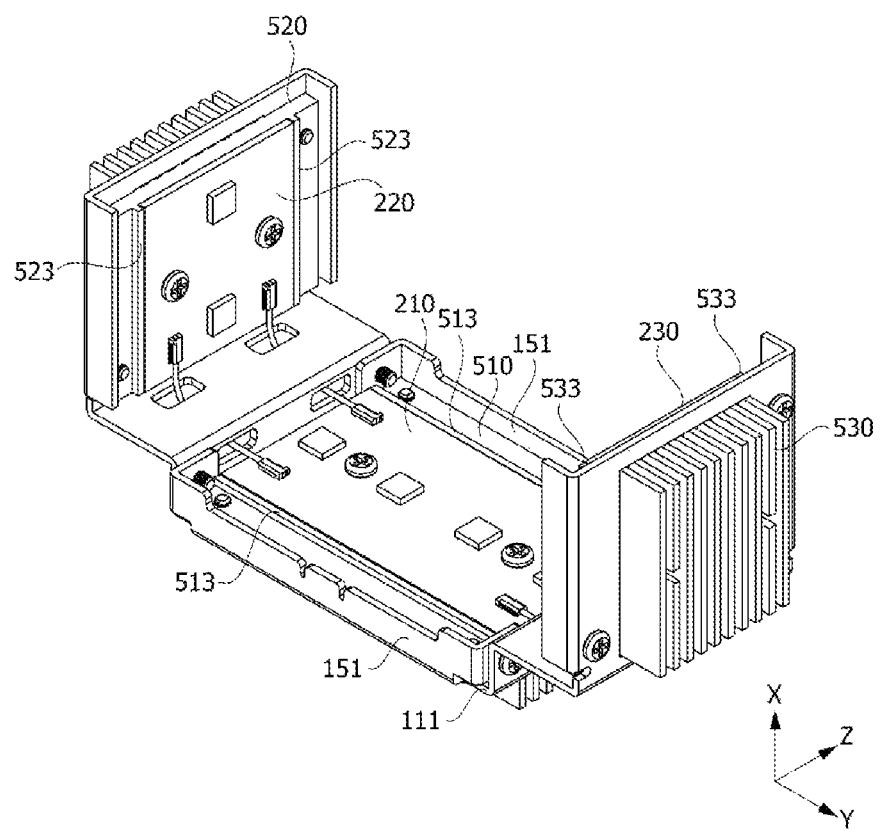

[FIG. 9]
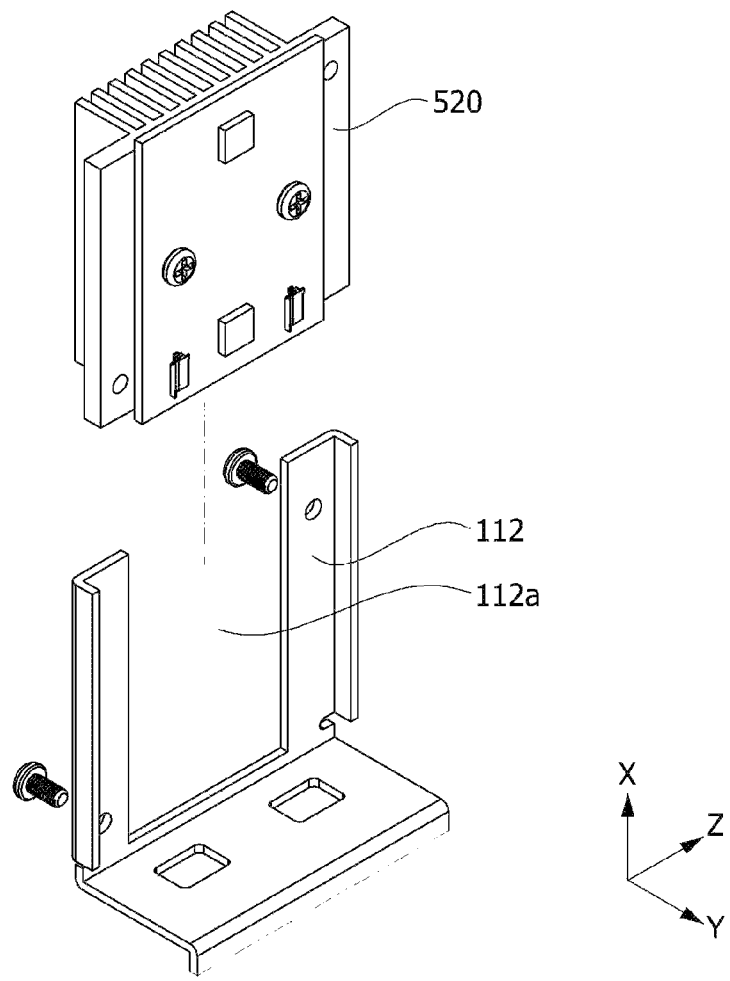

[FIG. 10]
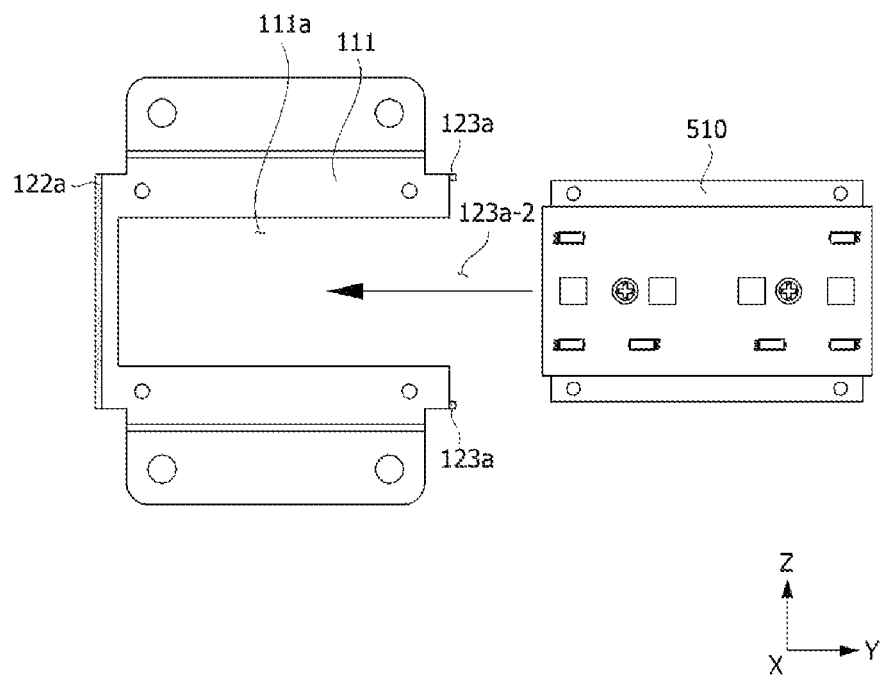

[FIG. 11]
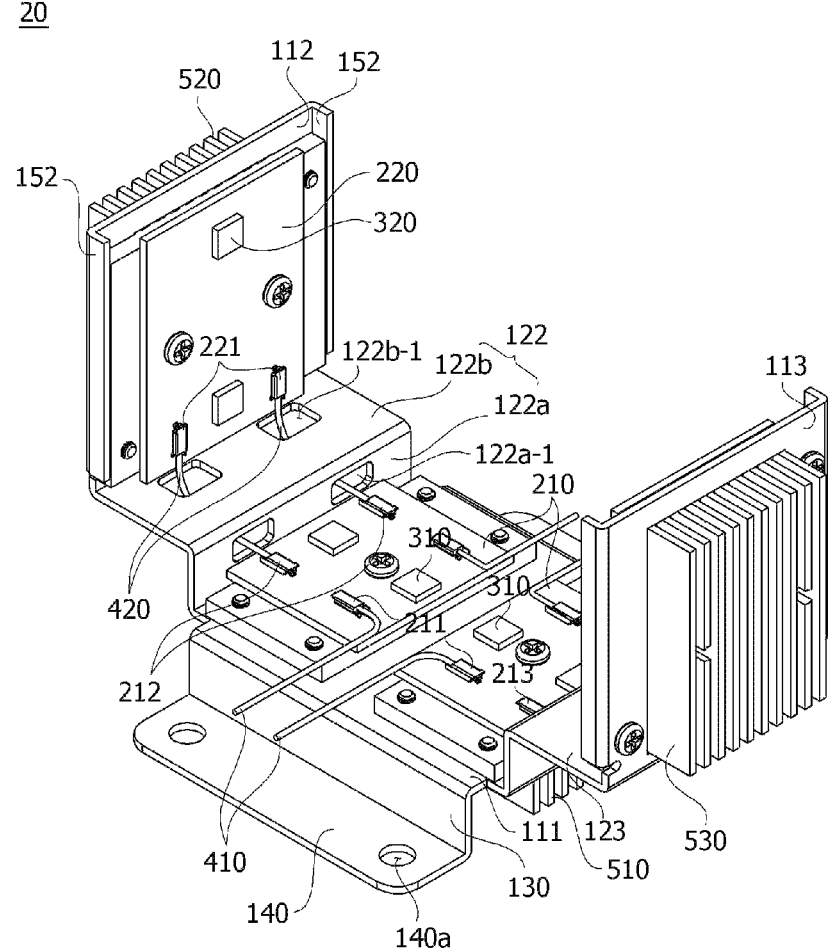

STERILIZATION DEVICE

CROSS REFERENCE TO RELATED APPLICATIONS

This application is the National Phase of PCT International Application No. PCT/KR2019/012189, filed on Sep. 20, 2019, which claims priority under 35 U.S.C. 119(a) to Patent Application No. 10-2018-0113331, filed in the Republic of Korea on Sep. 20, 2018, all of which are hereby expressly incorporated by reference into the present application.

TECHNICAL FIELD

The present invention relates to a sterilization device.

BACKGROUND ART

Escalators and moving walkways are installed in various places such as subway stations, airports, and department stores where there are large floating populations and are conveniently used by many people. However, handrails, which are safety devices of the escalators and the moving walkways have a problem of being easily exposed to germs.

Recently, devices which sterilize handrails using ultraviolet light emitting elements are being developed. The ultraviolet light emitting elements may output light (UV-A) in a near ultraviolet light wavelength range, light (UV-B) in a middle ultraviolet light wavelength range, and also light (UV-C) in a far ultraviolet light wavelength range. Among them, the light (UV-C) in the far ultraviolet wavelength range is known to have a sterilizing function.

Since users generally move while holding handrails, side surfaces of the handrails can also be easily exposed to germs. Accordingly, the side surfaces of the handrails also need to be sterilized.

In addition, since power cables and the like can be cured by ultraviolet light, methods to prevent the curing are required.

In addition, since the ultraviolet light emitting elements may have problems of reducing an amount of light due to foreign material contamination, periodic maintenance is required. Accordingly, in order to improve product installation and convenience of after service (A/S) such as cleaning, it is necessary to adopt a structure which facilitates assembly and disassembly.

Technical Problem

The present invention is directed to providing a sterilization device which sterilizes not only a top surface but also side surfaces of a handrail.

The present invention is directed to providing a sterilization device which suppresses a power cable and the like from being cured by ultraviolet light.

The present invention is directed to providing a sterilization device of which an ultraviolet light emitting element is easily disassembled and assembled.

Objectives to be solved by embodiments are not limited thereto and may include objectives or effects which can be understood from solutions of the objectives or the embodiments which will be described below.

Technical Solution

One aspect of the present invention provides a sterilization device including a frame including a first coupling part, a second coupling part, and a first connection part which connects the first coupling part and the second coupling part, a first circuit board disposed on the first coupling part, a second circuit board disposed on the second coupling part, a first ultraviolet light emitting element disposed on one surface of the first circuit board to be directed in a first direction, a second ultraviolet light emitting element disposed on one surface of the second circuit board to be directed in a second direction intersecting the first direction, and a first wiring part which is connected to the second circuit board and through which power is supplied to the second circuit board, wherein the first connection part includes a first through-hole through which the first wiring part passes.

The first wiring part may be connected to the first circuit board, and the first connection part may include a second through-hole through which the first wiring part passes.

The sterilization device may further include a second wiring part which is connected to the first circuit board and through which power is supplied to the first circuit board.

The first connection part may be bent from the first coupling part and the second coupling part.

The first connection part may include a first-1 connection part and a first-2 connection part connected to the first-1 connection part, the first-1 connection part may be bent from the first coupling part, and the first-2 connection part may be bent from the second coupling part.

The first through-hole may be disposed in the first-2 connection part, and the second through-hole may be disposed in the first-1 connection part.

The sterilization device may further include a first heat radiation member disposed on the other surface opposite to the one surface of the first circuit board, wherein the first coupling part may include a first opening in which the first heat radiation member is disposed.

The frame may include a pair of supports bent from the first coupling part, and the first heat radiation member may be disposed between the pair of supports.

The frame may include a pair of fixing parts bent from the pair of supports.

The fixing part may include a coupling hole.

A height in the first direction from the first coupling part to an end portion, which is disposed in a direction opposite to the first direction, of the first heat radiation member may be smaller than a height in the first direction from the first coupling part to an end portion, which is disposed in the direction opposite to the first direction, of the support.

The first heat radiation member may include a plurality of heat radiation fins disposed between the pair of supports, wherein the plurality of heat radiation fins may be disposed to be spaced apart from each other in a third direction.

The sterilization device may further include a second heat radiation member disposed on the other surface opposite to the one surface of the second circuit board, wherein the second coupling part may include a second opening in which the second heat radiation member is disposed.

The frame may include a pair of second guides bent from the second coupling part, and the second heat radiation member may be disposed between the pair of second guides.

The sterilization device may further include a third circuit board, a third ultraviolet light emitting element disposed on one surface of the third circuit board to face the second ultraviolet light emitting element, and a third wiring part connected to the third circuit board, wherein the frame may include a third coupling part and a second connection part which connects the first coupling part and the third coupling part, the third circuit board may be disposed on the third coupling part, and the second connection part may include a third through-hole through which the third wiring part passes.

The sterilization may further include a third heat radiation member disposed on the other surface opposite to the one surface of the third circuit board, wherein the third coupling part may include a third opening in which the third heat radiation member is disposed.

The frame may include a pair of third guides bent from the third coupling part, and the third heat radiation member may be disposed between the pair of third guides.

Another aspect of the present invention provides a sterilization device including a frame including a first coupling part, a second coupling part, and a first connection part which connects the first coupling part and the second coupling part, a first circuit board disposed on the first coupling part, a second circuit board disposed on the second coupling part, a first ultraviolet light emitting element disposed on one surface of the first circuit board to be directed in a first direction, a second ultraviolet light emitting element disposed on one surface of the second circuit board to be directed in a second direction intersecting the first direction, a first wiring part which is connected to the second circuit board and through which power is supplied to the second circuit board, a first heat radiation member disposed on the other surface opposite to the one surface of the first circuit board, and a second heat radiation member disposed on the other surface opposite to the one surface of the second circuit board, wherein the first coupling part and the second coupling part respectively include a first opening and a second opening, and the first heat radiation member and the second heat radiation member are respectively disposed in the first opening and the second opening.

The frame may include a pair of second guides bent from the second coupling part in the second direction.

The first coupling part may include a first-1 coupling hole, and the first heat radiation member may include a first-2 coupling hole corresponding to the first-1 coupling hole.

Advantageous Effects

According to embodiments, a sterilization device can sterilize not only a top surface but also side surfaces of a handrail using a second ultraviolet light emitting element.

In addition, curing of a wiring part due to ultraviolet light can be suppressed by blocking the ultraviolet light using a connection part.

In addition, since a heat radiation member can be coupled to an ultraviolet light emitting element in an insertion-coupling or sliding-coupling manner using a through-hole, assembly and disassembly can be facilitated.

Various useful advantages and effects of the present invention are not limited to the above-described contents and will be more easily understood while specific embodiments of the present invention are described.

DESCRIPTION OF DRAWINGS

FIG. 1 is a perspective view illustrating a target structure.
FIG. 2 is a perspective view illustrating a state in which a sterilization device is installed on the target structure of FIG. 1.
FIG. 3 is a perspective view illustrating the sterilization device of FIG. 2.
FIG. 4 is an exploded perspective view of FIG. 3.
FIG. 5 is a front view of FIG. 3.
FIG. 6 is a side view of FIG. 3.
FIG. 7 is a plan view of FIG. 3.
FIG. 8 is a view illustrating a modified example of FIG. 3.
FIGS. 9 and 10 are views illustrating other modified examples of FIG. 3.
FIG. 11 is a view illustrating still another modified example of FIG. 3.

MODES OF THE INVENTION

Hereinafter, exemplary embodiments of the present invention will be described in detail with reference to the accompanying drawings.

However, the technical spirit of the present invention is not limited to some embodiments which will be described and may be realized using various other embodiments, and at least one component of the embodiments may be selectively coupled, substituted, and used to realize the technical spirit within the range of the technical spirit.

In addition, unless clearly and specifically defined otherwise, all terms (including technical and scientific terms) used herein can be interpreted as having customary meanings to those skilled in the art, and meanings of generally used terms, such as those defined in commonly used dictionaries, will be interpreted by considering contextual meanings of the related technology.

In addition, the terms used in the embodiments of the present invention are considered in a descriptive sense and not to limit the present invention.

In the present specification, unless clearly indicated otherwise by the context, singular forms include the plural forms thereof, and in a case in which "at least one (or one or more) among A, B, and C" is described, this may include at least one combination among all possible combinations of A, B, and C.

In addition, in descriptions of components of the present invention, terms such as "first," "second," "A," "B," "(a)," and "(b)" can be used.

The terms are only to distinguish one element from another element, and an essence, order, and the like of the element are not limited by the terms.

In addition, it should be understood that, when an element is referred to as being "connected or coupled" to another element, such a description may include both a case in which the element is directly connected or coupled to another element and a case in which the element is connected or coupled to another element with still another element disposed therebetween.

In addition, in a case in which any one element is described as being formed or disposed "on or under" another element, such a description includes both a case in which the two elements are formed or disposed in direct contact with each other and a case in which one or more other elements are interposed between the two elements. In addition, when one element is described as being disposed "on or under" another element, such a description may include a case in which the one element is disposed at an upper side or a lower side with respect to another element.

FIG. 1 is a perspective view illustrating a target structure, and FIG. 2 is a perspective view illustrating a state in which a sterilization device is installed on the target structure of FIG. 1.

Referring to FIG. 1, a target structure 10 may include one of various structures such as an escalator and a moving walkway configured to transfer users to a predetermined location.

The target structure 10 may include a moving structure 11, and a housing 13 having an inner space where the moving structure 11 enters and exits. The moving structure 11 may refer to a handrail provided on the escalator or the moving walkway but is not necessarily limited thereto. Hereinafter, for the sake of convenience in the description, the moving structure 11 will be described in the case of the handrail of the escalator or the moving walkway.

Referring to FIG. 2, a sterilization device 20 according to the embodiment of the present invention may be fixed to the housing 13 of the target structure by coupling members (not shown) such as bolts and the like. In this case, the sterilization device 20 may be disposed in the housing 13. However, the sterilization device 20 is not necessarily limited thereto and may be fixed to another component of the target structure or fixed to be exposed to the outside of the housing 13.

FIG. 3 is a perspective view illustrating the sterilization device of FIG. 2, and FIG. 4 is an exploded perspective view of FIG. 3.

Referring to FIGS. 3 and 4, the sterilization device 20 may include a frame 100, a first circuit board 210, a second circuit board 220, a third circuit board 230, first ultraviolet light emitting elements 310, second ultraviolet light emitting elements 320, third ultraviolet light emitting elements 330, first wiring parts 420, second wiring parts 410, and third wiring parts 430. In this case, the third circuit board 230 and the third ultraviolet light emitting element 330 may be omitted as necessary.

In addition, the sterilization device 20 may further include a first heat radiation member 510, a second heat radiation member 520 and/or a third heat radiation member 530.

The frame 100 may include a first coupling part 111 and a second coupling part 112. The frame 100 may further include a third coupling part 113. The second coupling part 112 and the third coupling part 113 may be disposed to face each other.

The first coupling part 111 and the second coupling part 112 may be connected through a first connection part 122, and the first coupling part 111 and the third coupling part 113 may be connected through a second connection part 123.

The first connection part 122 may include a first-1 connection part 122a connected to the first coupling part 111 and a first-2 connection part 122b which connects the second coupling part 112 and the first-1 connection part 122a. The first-1 connection part 122a may be bent vertically upward from the first coupling part 111, and the first-2 connection part 122b may be horizontally bent from the first-1 connection part 122a.

The second connection part 123 may include a second-1 connection part 123a connected to the first coupling part 111 and a second-2 connection part 123b which connects the third coupling part 113 and the second-1 connection part 123a. The second-1 connection part 123a may be bent vertically upward from the first coupling part 111, and the second-2 connection part 123b may be horizontally bent from the second-1 connection part 123a.

The frame 100 may include a pair of supports 130 connected to the first coupling part 111. The pair of supports 130 may be formed to be bent vertically downward from the first coupling part 111.

A fixing part 140 may be connected to each of the supports 130. The fixing part 140 may include coupling holes 140a passing through the fixing part 140. Accordingly, the sterilization device 20 may be fixed to the housing or the like of the target structure by the coupling members such as bolts and the like inserted into the coupling holes 140a.

However, the sterilization device 20 is not necessarily limited thereto, a clamp and the like may be used as a coupling structure thereof.

The frame 100 may include a steel-based material, and the frame 100 may be formed through a press forming method but is not necessarily limited thereto.

The first circuit board 210 may be disposed on the first coupling part 111, the second circuit board 220 may be disposed on the second coupling part 112, and the third circuit board 230 may be disposed on the third coupling part 113.

The first ultraviolet light emitting element 310, the second ultraviolet light emitting element 320, and the third ultraviolet light emitting element 330 may be disposed on the first circuit board 210, the second circuit board 220, and the third circuit board 230, respectively.

Each of the first circuit board 210, the second circuit board 220, and the third circuit board 230 may include a metal printed circuit board (PCB). In addition, the first circuit board 210 may be coupled to the first heat radiation member 510 by coupling members such as bolts and the like, the second circuit board 220 may be coupled to the second heat radiation member 520 by coupling members such as bolts and the like, and the third circuit board 230 may be coupled to the third heat radiation member 530 by coupling members such as bolts and the like. Accordingly, the radiation performance of the first ultraviolet light emitting element 310, the second ultraviolet light emitting element 320, and the third ultraviolet light emitting element 330 may be improved.

A failure detection sensor (not shown) configured to detect whether a failure occurs at the corresponding circuit board may be disposed on each of the first circuit board 210, the second circuit board 220, and the third circuit board 230. A result of the failure detection sensor may be transmitted to a control server (not shown) or displayed through a display device (not shown).

The first ultraviolet light emitting element 310 may be disposed on the first circuit board 210, the second ultraviolet light emitting element 320 may be disposed on the second circuit board 220, and the third ultraviolet light emitting element 330 may be disposed on the third circuit board 230.

In the case in which the plurality of first ultraviolet light emitting elements 310 are provided, the plurality of first ultraviolet light emitting elements 310 may be disposed in a line. It is illustrated that four first ultraviolet light emitting elements 310 are disposed on the first circuit board 210 but is not necessarily limited thereto, and three or less or five or more first ultraviolet light emitting elements 310 may be disposed on the first circuit boards 210.

In the case in which the plurality of second ultraviolet light emitting elements 320 are provided, the plurality of second ultraviolet light emitting elements 320 may be disposed in a line. It is illustrated that two second ultraviolet light emitting elements 320 are disposed on the second circuit board 220 but is not necessarily limited thereto, and one or three or more second ultraviolet light emitting elements 320 may be disposed on the second circuit board 220.

In the case in which the plurality of third ultraviolet light emitting elements 330 are provided, the plurality of third ultraviolet light emitting elements 330 may be disposed in a line. It is illustrated that two third ultraviolet light emitting elements 330 are disposed on the third circuit board 230 but is not necessarily limited thereto, and one or three or more third ultraviolet light emitting elements 330 may be disposed on the third circuit board 230.

Each of the first ultraviolet light emitting element 310, the second ultraviolet light emitting element 320, and the third ultraviolet light emitting element 330 may emit ultraviolet light. In the present specification, the ultraviolet light emitting element may be used with a meaning including an ultraviolet light emitting element package including a reflective member, a transparent member, or the like in addition to the ultraviolet light emitting element.

Each of the first ultraviolet light emitting element 310, the second ultraviolet light emitting element 320, and the third ultraviolet light emitting element 330 may also emit light (UV-A) in a near ultraviolet light wavelength range, light (UV-B) in a middle ultraviolet light wavelength range, and light (UV-C) in a far ultraviolet light wavelength range. The light wavelength range may be determined according to a composition ratio of Al in a semiconductor structure.

For example, the light (UV-A) in the near ultraviolet light wavelength range may have a peak wavelength in the range of 320 nm to 420 nm, the light (UV-B) in the middle ultraviolet light wavelength range may have a peak wavelength in the range of 280 nm to 320 nm, and the light (UV-C) in the far ultraviolet light wavelength range may have a peak wavelength in the range of 100 nm to 280 nm. The ultraviolet light emitting element may be a light-emitting diode (LED) or an organic LED (OLED) but is not limited thereto.

The second wiring part 410 may be electrically connected to the first circuit board 210 so that power needed for the first ultraviolet light emitting element 310 to emit light may be supplied therethrough.

To this end, first-1 connectors 211 to which one ends of the second wiring parts 410 are detachably coupled may be disposed on the first circuit board 210, and the other ends of the second wiring part 410 may be electrically connected to a power supply module (not shown) configured to supply power needed to drive the handrail.

The first wiring parts 420 may be electrically connected to the second circuit board 220 so that power needed for the second ultraviolet light emitting element 320 emit light may be supplied therethrough.

The first wiring parts 420 may also connect the first circuit board 210 and the second circuit board 220. To this end, second connectors 221 to which one ends of the first wiring parts 420 are detachably coupled may be disposed on the second circuit board 220, and first-2 connectors 212 to which the other ends of the first wiring parts 420 are detachably coupled may be disposed on the first circuit board 210. However, the present invention is not necessarily limited thereto, and the other ends of the first wiring parts 420 may be directly coupled to the power supply module (not shown) configured to supply power needed to drive the handrail. That is, the second circuit board 220 may be connected to the first circuit board 210 in series or parallel with respect to the power supply module.

In the case in which the first wiring parts 420 are directly connected to the power supply module, the first wiring parts 420 may pass through first through-holes 122b-1 of the first-2 connection parts 122b, and in the case in which the first wiring parts 420 are connected to the first circuit board 210, the first wiring parts 420 may sequentially pass through second through-holes 122a-1 of the first-1 connection part 122a and the first through-holes 122b-1 of the first-2 connection part 122b. Accordingly, the first wiring parts 420 may be suppressed from being cured due to ultraviolet light.

The third wiring parts 430 (see FIG. 5) may be electrically connected to the third circuit board 230 so that power needed for the third ultraviolet light emitting element 330 to emit light may be supplied therethrough.

The third wiring parts 430 may also connect the first circuit board 210 and the third circuit board 230. To this end, third connectors 231 to which one ends of the third wiring parts 430 are detachably coupled may be disposed on the third circuit board 230, and first-3 connectors 213 detachably coupled to other ends of the third wiring parts 430 may be disposed on the first circuit board 210. However, the present invention is not necessarily limited thereto, and the other ends of the third wiring parts 430 may be directly connected to the power supply module (not shown) configured to supply power needed to drive the handrail. That is, the third circuit board 230 may be coupled to the first circuit board 210 in series or parallel with respect to the power supply module.

In the case in which the third wiring parts 430 are directly connected to the power supply module, the third wiring parts 430 may pass through third through-holes 123b-1 of the second-2 connection part 123b, and in the case in which the third wiring parts 430 are connected to the first circuit board 210, the third wiring parts 430 may sequentially pass through the through-holes 123a-1 of the second-1 connection part 123a and the third through-holes 123b-1 of the second-2 connection part 123b. Accordingly, the third wiring part 420 may be suppressed from being cured due to ultraviolet light.

Each of the first-1 connector 211, the first-2 connector 212, the first-3 connector 213, the second connector 221, and the third connector 231 may be a metal connector. Accordingly, the connectors and the like may be suppressed from being cured due to the ultraviolet light.

The first heat radiation member 510 may be coupled to the first coupling part 111 by coupling members such as bolts and the like. To this end, the first coupling part 111 may include first-1 coupling holes 111b, and the first heat radiation member 510 may include first-2 coupling holes 510a corresponding to the first-1 coupling holes 111b. Similarly, the second heat radiation member 520 may be coupled to the second coupling part 112 by coupling members such as bolts and the like, and the third heat radiation member 530 may be coupled to the third coupling part 113 by coupling members such as bolts and the like.

The first circuit board 210 may be coupled to one surface of the first heat radiation member 510, a plurality of heat radiation fins 511 passing through a first opening 111a of the first coupling part 111 may protrude from the other surface of the first heat radiation member 510.

The second circuit board 220 may be coupled to one surface of the second heat radiation member 520, and a plurality of heat radiation fins 521 passing through a second opening 112a of the second coupling part 112 may protrude from the other surface of the second heat radiation member 520. Meanwhile, when the second heat radiation member 520 is coupled thereto, a position or posture of the second heat radiation member 520 may be easily arranged by a pair of second guides 152 connected to the second coupling part 112.

The third circuit board 230 may be coupled to one surface of the third heat radiation member 530, and a plurality of heat radiation fins 531 passing through a third opening 113a of the third coupling part 113 may protrude from the other surface of the third heat radiation member 530. Meanwhile, when the third heat radiation member 530 is coupled thereto, a position or posture of the third heat radiation member 530 may be easily arranged by a pair of third guides 153 connected to the third coupling part 113.

Each of the first heat radiation member 510, the second heat radiation member 520, and the third heat radiation member 530 may include aluminum (Al) and may be manufactured through an extrusion process but is not necessarily limited thereto.

FIG. 5 is a front view of FIG. 3.

Referring to FIG. 5, the first ultraviolet light emitting element 310 may be disposed on the first circuit board 210 to be directed in an X-axis direction (first direction) so as to emit ultraviolet light on one surface of the moving structure 11.

The second ultraviolet light emitting element 320 may be disposed on the second circuit board 220 to be directed in a Y-axis direction (second direction), and the third ultraviolet light emitting element 330 may be disposed on the third circuit board 230 to be directed in a direction opposite to the Y-axis direction. The Y-axis direction may be a direction intersecting the X-axis direction. The Y-axis direction may be a direction perpendicular to the X-axis direction but is not necessarily limited thereto.

The second ultraviolet light emitting element 320 and the third ultraviolet light emitting element 330 may be disposed with the moving structure 11 interposed therebetween in the Y-axis direction. Accordingly, the second ultraviolet light emitting element 320 and the third ultraviolet light emitting element 330 may emit ultraviolet light to both side surfaces of the moving structure 11.

The first-1 connection part 122a and the second-1 connection part 123a may be bent from both ends, which are disposed in a direction parallel to the Y-axis direction, of the first coupling part 111 to extend in the X-axis direction.

The first-2 connection part 122b may be bent from an end portion, which is disposed in a direction opposite to the X-axis direction, of the second coupling part 112 to extend in the Y-axis direction. Accordingly, an ultraviolet light blocking area may be formed by the first connection part 122, and the first wiring part 420 may be disposed in the ultraviolet light blocking area formed by the first connection part 122.

The second-2 connection part 123b may be bent from an end portion, which is disposed in the direction opposite to the X-axis direction, of the third coupling part 113 to the direction opposite to the Y-axis direction. Accordingly, an ultraviolet light blocking area may be formed by the second connection part 123, and the third wiring part 430 may be disposed in the ultraviolet light blocking area formed by the second connection part 123.

The first heat radiation member 510 may be disposed on the first circuit board 210 to be directed in the direction opposite to the X-axis direction, the second heat radiation member 520 may be disposed on the second circuit board 220 to be directed in the direction opposite to the Y-axis direction, and the third heat radiation member 530 may be disposed on the third circuit board 230 to be directed in the Y-axis direction.

FIG. 6 is a side view of FIG. 3.

Referring to FIG. 6, the pair of supports 130 may be disposed to face each other in a Z-axis direction. The Z-axis direction (third direction) may be a direction perpendicular to the X-axis direction and the Y-axis direction.

The pair of supports 130 may be bent from both ends, which are disposed in a direction parallel to the Z-axis direction, of the first coupling part 111 to extend in the direction opposite to the X-axis direction.

A pair of fixing parts 130 may be bent from end portions, which are disposed in the direction opposite to the X-axis direction, of the pair of supports 130 to extend in directions parallel to the Z-axis direction, that is, directions, in which the pair of fixing parts 140 move away from each other, among the directions.

The heat radiation fins 511 of the first heat radiation member 510 may be disposed between the pair of supports 130. In this case, the plurality of heat radiation fins 511 may be disposed to be spaced apart from each other in the Z-axis direction like the pair of supports 130. Similarly, the heat radiation fins 521 and the heat radiation fins 531 of the second heat radiation member 520 and the third heat radiation member 530 may be disposed to be spaced apart from each other in the Z-axis direction. Accordingly, heat radiation performance due to natural convection may be improved.

A protruding length of the heat radiation fin 511, for example, a height H1 in the X-axis direction from the first coupling part 111 to an end portion, which is disposed in the direction opposite to the X-axis direction, of the first heat radiation member 510 may be smaller than, for example, a height H2 in the X-axis direction from the first coupling part 111 to an end portion, which is disposed in the direction opposite to the X-axis direction, of the support 130.

FIG. 7 is a plan view of FIG. 3.

Referring to FIG. 7, a power supply module 600 is illustrated in the drawing. The power supply module 600 may be electrically connected to the first circuit board 210 through the second wiring parts 410 to supply power needed for the ultraviolet light emitting element to emit light. The power supply module 600 may be an external power source configured to supply power to the handrail but is not necessarily limited thereto.

The pair of second guides 152 may be bent from both ends, which are disposed in the direction parallel to the Z-axis direction, of the second coupling part 112 to extend in the Y-axis direction.

The pair of second guides 152 may be disposed to face each other in the Z-axis direction to support both ends, which are disposed in the direction parallel to the Z-axis direction, of the second heat radiation member 520. Accordingly, a posture of the second heat radiation member 520 may be easily arranged before the second heat radiation member 520 is coupled by the coupling members such as the bolts and the like.

The pair of third guides 153 may be bent from both ends, which are disposed in the direction parallel to the Z-axis direction, of the third coupling part 113 to extend in the direction opposite to the Y-axis direction.

The pair of third guides 153 may be disposed to face each other in the Z-axis direction to support both ends, which are disposed in the direction parallel to the Z-axis direction, of the third heat radiation member 530. Accordingly, a posture of the third heat radiation member 530 may be easily arranged before the third heat radiation member 530 is coupled by the coupling members such as the bolts and the like.

FIG. 8 is a view illustrating a modified example of FIG. 3.

Referring to FIG. 8, a pair of first guides 151 instead of the pair of supports may be connected to the first coupling part 111.

The pair of first guides 151 may be bent from both ends, which are disposed in the direction parallel to the Z-axis direction, of the first coupling part 111 to extend in the X-axis direction.

The pair of first guides 151 may be disposed to face each other in the Z-axis direction and may support both ends, which are disposed in the direction parallel to the Z-axis direction, of the first heat radiation member 510. Accordingly, a posture of the first heat radiation member 510 may be easily arranged before the first heat radiation member 510 is coupled by the coupling members such as the bolts and the like.

The first heat radiation member 510, the second heat radiation member 520, and the third heat radiation member 530 may respectively include pairs of guide protrusions 513, 523, and 533 disposed to face each other in the Z-axis direction to support both ends, which are disposed in the Z-axis direction, of the first circuit board 210, the second circuit board 220, and the third circuit board 230. Accordingly, a posture of each of the first circuit board 210, the second circuit board 220, and the third circuit board 230 may be easily arranged before each of the first circuit board 210, the second circuit board 220, and the third circuit board 230 is coupled by the coupling members such as the bolts and the like.

FIGS. 9 and 10 are views illustrating other modified examples of FIG. 3.

Referring to FIG. 9, the second opening 112a may be formed in one end surface, which is disposed in the X-axis direction, of the second coupling part 112. Accordingly, the second heat radiation member 520 may be slidably moved and inserted into the second opening 112a in the direction opposite to the X-axis direction, and thus assembly and disassembly may be facilitated.

Referring to FIG. 10, the first opening 111a may be formed in one end surface, which is disposed in the Y-axis direction, of the first coupling part 111. Accordingly, the first heat radiation member 510 may be slidably moved and inserted into the first opening 111a in the direction opposite to the Y-axis direction, and thus assembly and disassembly may be facilitated. In this case, the second-1 connection part 123a may include a through-hole 123a-2 which is connected to the first opening 111a to allow the first heat radiation member 510 to enter and exit. A width of the through-hole 123a-2 may be greater than a width of the first opening 111a and a maximum width of the first heat radiation member 510.

However, the present invention is not necessarily limited thereto, and the first opening 111a may also be formed in one end surface, which is disposed in the Z-axis direction, of the first coupling part 111. In this case, the first heat radiation member 510 may be slidably moved and inserted into the first opening 111a in a direction opposite to the Z-axis direction, and the support may include a through-hole connected to the first opening 111a to allow the first heat radiation member 510 to enter and exit.

FIG. 11 is a view illustrating still another modified example of FIG. 3.

Referring to FIG. 11, a pair of first circuit boards 210 may be disposed on the first coupling part 111. Accordingly, the first circuit boards 210, the second circuit board 220, and the third circuit board 230 may be formed using circuit boards on which the same number of, for example, two ultraviolet light emitting elements, are disposed and which have the same size (see FIG. 4).

In this case, the first heat radiation member 510 may also be coupled to each of the first circuit boards 210, and the first coupling part 111 may include a pair of first openings 111a (see FIG. 4) into which the pair of first heat radiation members 510 are inserted. In addition, the second circuit board 220 may be connected one of the pair of first circuit boards 210, and the third circuit board 230 may be connected to the remaining one of the pair of first circuit boards 210. The pair of first circuit boards 210 may be coupled in parallel with respect to the power supply module 600 (see FIG. 7) but are not necessarily limited thereto and may be connected in series with respect to the power supply module 600.

While the present invention has been mainly described above with reference to the embodiments, it will be understood by those skilled in the art that the invention is not limited to the embodiments, the embodiments are only examples, and various modifications and applications which are not illustrated above may fall within the range of the present invention without departing from the essential features of the present embodiments. For example, components specifically described in the embodiments may be modified and implemented. In addition, it should be understood that differences related to modifications and applications fall within the scope of the present invention defined by the appended claims.

The invention claimed is:

1. A sterilization device comprising:
a frame including a first coupling part, a second coupling part, and a first connection part which connects the first coupling part and the second coupling part;
a first circuit board disposed on the first coupling part;
a second circuit board disposed on the second coupling part;
a first ultraviolet light emitting element disposed on one surface of the first circuit board to be directed in a first direction;
a second ultraviolet light emitting element disposed on one surface of the second circuit board to be directed in a second direction intersecting the first direction; and
a first wiring part which is connected to the second circuit board and through which power is supplied to the second circuit board,
wherein the first connection part includes:
a first through-hole through which the first wiring part passes;
a first-1 connection part connected to the first coupling part; and
a first-2 connection part connected to the second coupling part and the first-1 connection part, the first-1 connection part and the first-2 connection part forming a stepped structure between the first coupling part and the second coupling part.

2. The sterilization device of claim 1, wherein:
the first wiring part is connected to the first circuit board; and
the first connection part includes a second through-hole through which the first wiring part passes.

3. The sterilization device of claim 1, further comprising a second wiring part which is connected to the first circuit board and through which power is supplied to the first circuit board.

4. The sterilization device of claim 2, wherein the first connection part is bent from the first coupling part and the second coupling part.

5. The sterilization device of claim 4, wherein:
the first-1 connection part is bent from the first coupling part; and
the first-2 connection part is bent from the second coupling part.

6. The sterilization device of claim 5, wherein:
the first through-hole is disposed in the first-2 connection part; and
the second through-hole is disposed in the first-1 connection part.

7. The sterilization device of claim 4, further comprising:
a first heat radiation member disposed on the other surface opposite to the one surface of the first circuit board,
wherein the first coupling part includes a first opening in which the first heat radiation member is disposed.

8. The sterilization device of claim 7, wherein:
the frame includes a pair of supports bent from the first coupling part; and
the first heat radiation member is disposed between the pair of supports.

9. The sterilization device of claim 8, wherein the frame includes a pair of fixing parts bent from the pair of supports.

10. The sterilization device of claim 9, wherein the fixing part includes a coupling hole.

11. The sterilization device of claim 8, wherein a height in the first direction from the first coupling part to an end portion, which is disposed in a direction opposite to the first direction, of the first heat radiation member is smaller than a height in the first direction from the first coupling part to an end portion, which is disposed in the direction opposite to the first direction, of the support.

12. The sterilization device of claim 8, wherein the first heat radiation member includes a plurality of heat radiation fins disposed between the pair of supports,
wherein the plurality of heat radiation fins are disposed to be spaced apart from each other in a third direction perpendicular to the first direction and the second direction.

13. The sterilization device of claim 7, further comprising a second heat radiation member disposed on the other surface opposite to the one surface of the second circuit board,
wherein the second coupling part includes a second opening in which the second heat radiation member is disposed.

14. The sterilization device of claim 13, wherein:
the frame includes a pair of second guides bent from the second coupling part; and
the second heat radiation member is disposed between the pair of second guides.

15. The sterilization device of claim 4, further comprising:
a third circuit board;
a third ultraviolet light emitting element disposed on one surface of the third circuit board to face the second ultraviolet light emitting element; and
a third wiring part connected to the third circuit board,
wherein the frame includes a third coupling part and a second connection part which connects the first coupling part and the third coupling part,
the third circuit board is disposed on the third coupling part, and
the second connection part includes a third through-hole through which the third wiring part passes.

16. The sterilization device of claim 15, further comprising a third heat radiation member disposed on the other surface opposite to the one surface of the third circuit board,
wherein the third coupling part includes a third opening in which the third heat radiation member is disposed.

17. The sterilization device of claim 16, wherein:
the frame includes a pair of third guides bent from the third coupling part; and
the third heat radiation member is disposed between the pair of third guides.

18. A sterilization device comprising:
a frame including a first coupling part, a second coupling part, and a first connection part which connects the first coupling part and the second coupling part;
a first circuit board disposed on the first coupling part;
a second circuit board disposed on the second coupling part;
a first ultraviolet light emitting element disposed on one surface of the first circuit board to be directed in a first direction;
a second ultraviolet light emitting element disposed on one surface of the second circuit board to be directed in a second direction intersecting the first direction;
a first wiring part which is connected to the second circuit board and through which power is supplied to the second circuit board;
a first heat radiation member disposed on the other surface opposite to the one surface of the first circuit board; and
a second heat radiation member disposed on the other surface opposite to the one surface of the second circuit board,
wherein the first coupling part and the second coupling part respectively include a first opening and a second opening, and
the first heat radiation member and the second heat radiation member are disposed in the first opening and the second opening, respectively.

19. The sterilization device of claim 18, wherein the frame includes a pair of second guides bent from the second coupling part in the second direction.

20. The sterilization device of claim 19, wherein:
the first coupling part includes a first-1 coupling hole; and
the first heat radiation member includes a first-2 coupling hole corresponding to the first-1 coupling hole.

* * * * *